United States Patent [19]

Meuwly et al.

[11] Patent Number: 5,185,445
[45] Date of Patent: Feb. 9, 1993

[54] SILYLATED 2-(2-HYDROXYPHENYL)-4,6-DIARYL-1,3,5-TRIAZINES

[75] Inventors: Roger Meuwly, Marly; Mario Slongo, Tafers, both of Switzerland; Andreas Valet, Eimeldingen, Fed. Rep. of Germany

[73] Assignee: Ciba-Geigy Corporation, Ardsley, N.Y.

[21] Appl. No.: 843,118

[22] Filed: Feb. 27, 1992

[30] Foreign Application Priority Data

Mar. 5, 1991 [CH] Switzerland .............................. 655/91

[51] Int. Cl.⁵ ............................................ C07D 251/24
[52] U.S. Cl. ....................................................... 544/216
[58] Field of Search ........................................ 544/216

[56] References Cited

FOREIGN PATENT DOCUMENTS 0339262 11/1989 European Pat. Off. .
0389427 9/1990 European Pat. Off. .
0461071 12/1991 European Pat. Off. .

Primary Examiner—John M. Ford
Attorney, Agent, or Firm—Luther A. R. Hall

[57] ABSTRACT

2-(2-Hydroxyphenyl)-4,6-diaryl-1,3,5-triazines, which carry in the 4-position of the 2-hydroxyphenyl radical a silyl group linked through oxygen to the phenyl nucleus, as well as condensation products whose $$+\mathrm{Si-O}+$$

units contain 2-(2-hydroxyphenyl)-4,6-diaryl-1,3,5-triazines in the side-chain, are UV absorbers which are suitable for use as stabilizers for organic polymers.

10 Claims, No Drawings

SILYLATED 2-(2-HYDROXYPHENYL)-4,6-DIARYL-1,3,5-TRIAZINES

The present invention relates to 2-hydroxyphenyl-s-triazines which carry a silicon-containing radical in the 4-position of the 2-hydroxyphenyl group, and to the use thereof as stabilisers for organic polymers.

2-(2-Hydroxyphenyl)-4,6-diaryl-1,3,5-triazines are UV absorbers and can therefore be used as light stabilisers. They usually carry an alkyl- or acyl-substituted hydroxyl group in the 4-position of the 2-hydroxyphenyl group (q.v. (U.S. Pat. Nos. 3,118,887, 3,249,608). It has been proposed to use such compounds especially for the light stabilisation of polymers. The UV absorber present in the outer layer of the mouldings made from such stabilised polymers prevents shortwave light from penetrating into the core of the moulding.

It has now been found that specific 2-hydroxyphenyl-s-triazines which carry a silicon group as substituent are particularly suitable light stabilisers. The triazines are novel compounds and have the formula Ia or Ib

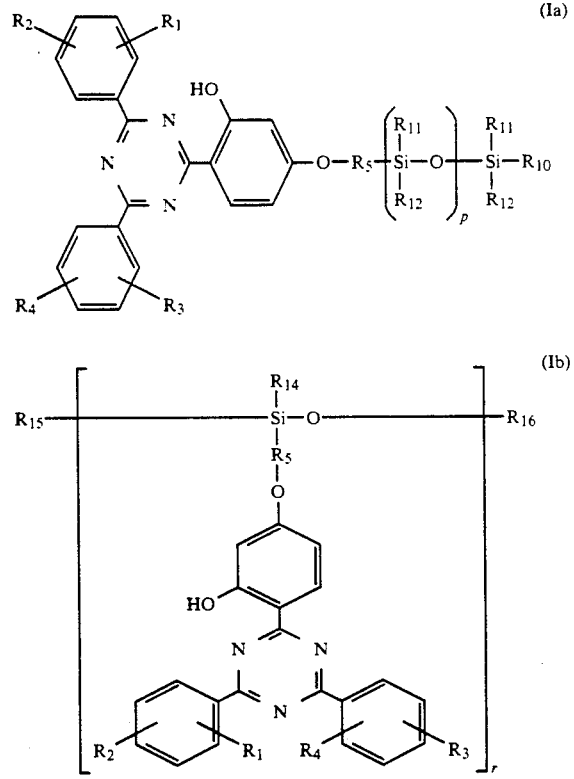

wherein p is 0 or an integer from 1–50, r is an integer from 1–50, $R_1$ and $R_3$ are each independently of the other hydrogen, OH, $C_1$-$C_{12}$alkyl or cyclohexyl, $R_2$ and $R_4$ are each independently of the other hydrogen, OH, $C_1$-$C_{12}$alkyl, $C_1$-$C_{18}$alkoxy, halogen or a group —O—II,

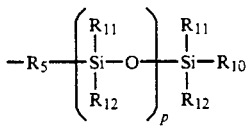

$R_5$ is a direct bond or a divalent group of one of the following formulae: $-C_mH_{2m}-$, $-(CH_2)_m-O-$, $-(CH_2)_m-O-R_6-$, $-(CH_2)_m-CO-X-(CH_2)_n-$, $-(CH_2)_m-CO-X-(CH_2)_n-O-$,

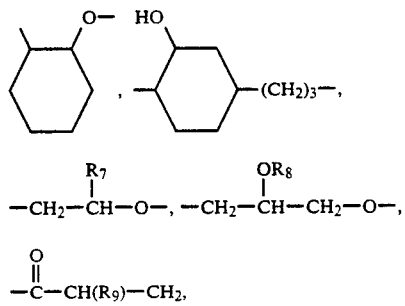

$-CH_2-CH(OH)-CH_2-Y-(CH_2)_m-$, wherein m and n are each independently of the other 1–4, $R_6$ is $C_1$-$C_{12}$alkylene, cyclohexylene or phenylene, $R_7$ is $C_1$-$C_{12}$alkyl, $C_5$-$C_8$cycloalkyl, phenyl, $C_2$-$C_{13}$alkoxymethyl, $C_6$-$C_9$cycloalkoxymethyl or phenoxymethyl, $R_8$ is a group of formula II, $R_9$ is hydrogen or methyl, X is —O— or —$NR_{13}$—, wherein $R_{13}$ is hydrogen, $C_1$-$C_{12}$alkyl, phenyl or a group —(CH$_2$)$_3$—II or —(CH$_2$)$_3$—O—II, Y is —O— or —NH—, $R_{10}$, $R_{11}$ and $R_{12}$ are each independently of one another $C_1$-$C_{18}$alkyl, cyclohexyl, phenyl or $C_1$-$C_{18}$alkoxy, and, if $R_2$ and $R_4$ are not a group —O—II, $R_{10}$ and/or $R_{11}$ may also be a group of formula III

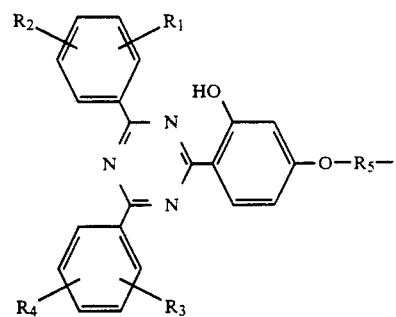

$R_{14}$ is $C_1$-$C_{12}$alkyl, $C_5$-$C_8$cycloalkyl or phenyl, and $R_{15}$ is hydroxy or $C_1$-$C_4$alkoxy and $R_{16}$ is hydrogen or $C_1$-$C_4$alkyl or, if r is greater than 2, $R_{15}$ and $R_{16}$ together may be a direct bond.

One of the substituents $R_1$, $R_2$, $R_3$, $R_4$, $R_7$, $R_8$ and $R_{14}$ in formula Ia or formula Ib as $C_1$-$C_{12}$alkyl may be a linear or branched alkyl group. Typical examples of such groups are methyl, ethyl, n-propyl, isopropyl, n-butyl, tert-butyl, pentyl, hexyl, octyl, 2-ethylhexyl, nonyl, decyl or dodecyl. $R_{10}$, $R_{11}$ and $R_{12}$ as $C_1$-$C_{18}$alkyl may additionally be tetradecyl, hexadecyl or octadecyl.

$R_7$ and $R_{14}$ as $C_5$-$C_8$cycloalkyl may be cyclopentyl, cyclohexyl or cyclooctyl, preferably cyclohexyl.

$R_2$, $R_4$, $R_{10}$, $R_{11}$ and $R_{12}$ as $C_1$-$C_{18}$alkoxy may be linear or branched alkoxy groups. Exemplary of such groups are methoxy, ethoxy, isopropoxy, butoxy, hexoxy, octyloxy, decyloxy, dodecyloxy or octadecyloxy.

$R_{10}$, $R_{11}$ and $R_{12}$ are preferably $C_1$-$C_4$alkyl or $C_1$-$C_4$alkoxy, and $R_{14}$ is preferably $C_1$-$C_4$alkyl.

$R_6$ as $C_1$-$C_{12}$alkylene may be a linear or branched alkylene group. Such groups are typically methylene, dimethylen, 1,2-propylene, trimethylene, 2,2-dimethyltrimethylene, tetramethylene, hexamethylene, octamethylene or dodecamethylene.

Preferred compounds of formula Ia are those wherein $R_5$ is a direct bond or a divalent group of one of the following formulae: $-(CH_2)_m-$, $-(CH_2)_m-O-$, $-(CH_2)_m-O-R_6-$, $-(CH_2)_m-CO-X-(CH_2)_n-$, $-(CH_2)_m-CO-X-(CH_2)_n-O-$,

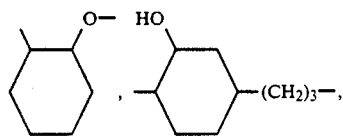

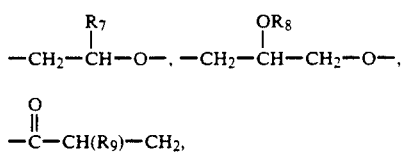

$-CH_2-CH(OH)-CH_2-Y-(CH_2)_m-$, wherein m and n are each independently of the other 1-4.

Also preferred are compounds of formula Ia or Ib wherein $R_1$, $R_2$, $R_3$ and $R_4$ are each independently of one another hydrogen or methyl. Especially preferred compounds are-(2-hydroxyphenyl)-s-triazines of formula Ia or formula Ib which are substituted in the 4- and 6-position by a phenyl, p-tolyl or 2,4-dimethylphenyl group.

The novel compounds preferably carry at the silicon atom $C_1$-$C_8$alkyl, phenyl or $C_1$-$C_8$alkoxy as substituents $R_{10}$, $R_{11}$ and $R_{12}$, and $C_1$-$C_8$alkyl or phenyl as $R_{14}$, or $R_{10}$ and/or $R_{11}$ is a group of formula III. Compounds wherein $R_{10}$, $R_{11}$ and $R_{12}$ are $C_1$-$C_4$alkyl or $C_1$-$C_4$alkoxy and $R_{14}$ is $C_1$-$C_4$alkyl are especially preferred.

The hydroxyphenyltriazine group is linked to the silyl radical through the group $R_5$.

Preferably $R_5$ is a group $-C_mH_{2m}-$, $-(CH_2)_m-O-$, $-(CH_2)_m-CO-X-(CH_2)_n-$,

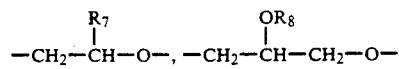

or $-CH_2-CH(OH)-CH_2-Y-(CH_2)_m-$, wherein m is 1, 2 or 3, $R_7$ is methyl, phenyl, $C_3$-$C_9$alkoxymethyl or phenoxymethyl, $R_8$ is a group of formula II and X and Y are each oxygen.

Particularly preferred compounds of formula Ia or Ib are those wherein $R_5$ is a group $-C_mH_{2m}-$, $-(CH_2)_2-O-$, $-CH_2-CO-O-CH_2-$, $-CH_2-CH(O-C_4H_9)-O-$,

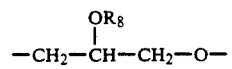

or $-CH_2-CH(OH)-CH_2-O-(CH_2)_3-$, m is an integer 1, 2 or 3, and $R_8$ is a radical

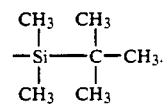

The compounds of formula Ia, wherein p is 0, are especially preferred.

Compounds of formula Ia or Ib, wherein $R_1$, $R_2$, $R_3$ and $R_4$ are each in o- and/or p-position, p is 0, $R_5$ is $-(CH_2)_3-$, $R_{10}$ is methyl or ethyl, $R_{11}$ and $R_{12}$ are ethyl or ethoxy, $R_{14}$ is methyl, $R_{15}$ is $-OH$, methoxy or ethoxy, $R_{16}$ is hydrogen, methyl or ethyl, and, if r is greater than 2, $R_{15}$ and $R_{16}$ together may be a direct bond, are also especially preferred.

The following compounds are representative examples of compounds of formula Ia:

Z—O—$(CH_2)_3$—Si$(CH_3)_3$;
Z—O—$(CH_2)_3$—Si$(C_4H_9)(CH_3)_2$;
Z—O—$(CH_2)_2$—O—Si$(C_6H_5)(CH_3)_2$;
Z—O—$(CH_2)_3$—O—$(CH_2)_3$—Si$(CH_3)(OCH_3)_2$;
Z—O—$(CH_2)_2$—O—$CH_2$—Si$(CH_3)_3$;
Z—O—$CH_2COO$—$(CH_2)_3$—Si$(C_2H_5)_3$;
Z—O—$CH_2CH_2CONH$—$(CH_2)_3$—Si$(C_3H_7)_3$;
Z—O—$CH_2COO$—$CH_2CH_2O$—Si$(C_6H_5)(CH_3)_2$;

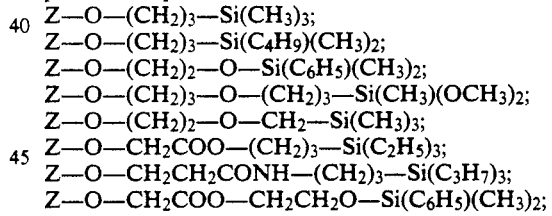

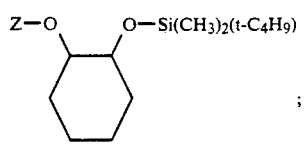 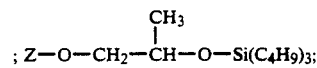

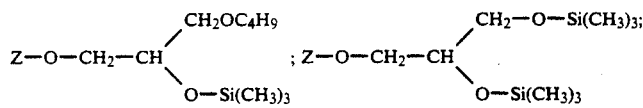

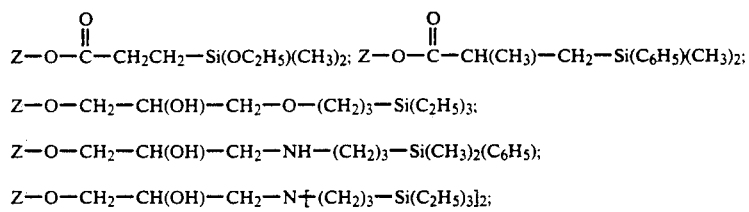

$$Z-O-CH_2CH_2O-\underset{\underset{CH_3}{|}}{\overset{\overset{CH_3}{|}}{Si}}-OCH_2CH_2-O-Z;$$

$$Z-O-CH_2CH(OH)CH_2-O-(CH_2)_3-\underset{\underset{C_6H_5}{|}}{\overset{\overset{CH_3}{|}}{Si}}-(CH_2)_3-O-CH_2CH(OH)CH_2-O-Z;$$

$$Z-O-(CH_2)_3-\underset{\underset{CH_3}{|}}{\overset{\overset{CH_3}{|}}{Si}}-O-Si(CH_3)_3;\ Z-O-(CH_2)_3-O-(CH_2)_3-Si(CH_3)_2-O-Si(CH_3)_3;$$

$$Z-O-CH_2CH_2COO-CH_2CH_2O-\underset{\underset{C_6H_5}{|}}{\overset{\overset{CH_3}{|}}{Si}}-O-\underset{\underset{C_6H_5}{|}}{\overset{\overset{CH_3}{|}}{Si}}-CH_3;$$

$$Z-O-CH_2-\overset{\overset{C_6H_5}{|}}{CH}-O-Si(CH_3)_2-O-Si-(CH_3)_2-O-\overset{\overset{C_6H_5}{|}}{CH}-CH-O-Z.$$

In the above formula, Z is a group

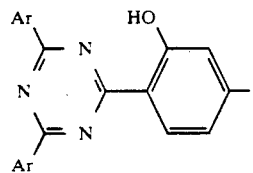

wherein Ar is phenyl, p-tolyl or 2,4-dimethylphenyl.

The synthesis of the compounds of formula Ia depends on the respective linking group $R_5$ through which the triazinyl group and the silyl group are attached. Possible syntheses are set out below for each type of $R_5$.

1) If $R_5$ is a group $-C_mH_{2m}-$:

$$AH + Cl-C_mH_{2m}-B \rightarrow Ia + HCl$$

wherein A is a triazine group of formula

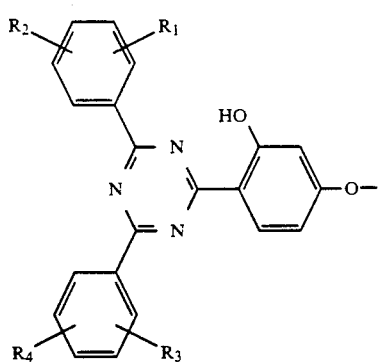

and B is a silyl group of formula

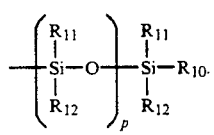

An alternative synthesis proceeds according to the scheme:

$$A-(CH_2)_{m-2}-CH=CH_2 + HB \rightarrow Ia$$

2) If $R_5$ is a group $-(CH_2)_m-O-$:

$$A-(CH_2)_m-OH + Cl-B \rightarrow Ia + HCl$$

3) If $R_5$ is a group $-(CH_2)_m-O-R_6-$:

$$A-(CH_2)_m-OH + Cl-R_6-B \rightarrow Ia + HCl$$

4) If $R_5$ is a group $-(CH_2)_m-CO-X-(CH_2)_n-$:

$$A-(CH_2)_m-COOR + HX-(CH_2)_n-B \rightarrow Ia + ROH$$

$$R = C_1-C_2 alkyl$$

5) If $R_5$ is a group $-(CH_2)_m-CO-X-(CH_2)_n-O-$:

$$A-(CH_2)_m-COOR + HX-(CH_2)_n-OH \longrightarrow$$

$$A-(CH_2)_m-CO-X-(CH_2)_n-OH \xrightarrow{+ClB} Ia + HCl$$

6) If $R_5$ is a group

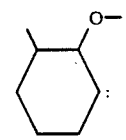

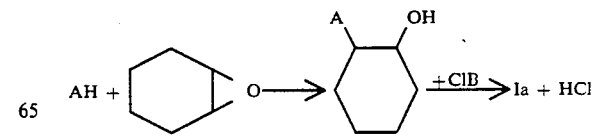

7) If $R_5$ is a group $-CH_2-CH(R_7)-O-$:

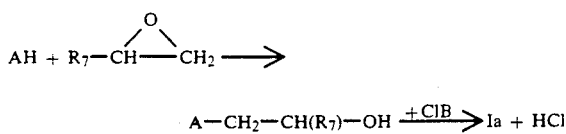

$$A-CH_2-CH(R_7)-OH \xrightarrow{+ClB} Ia + HCl$$

8) If $R_5$ is a group $-CH_2-CH(OR_8)-CH_2O-$:

$$AH + ClCH_2CH(OH)CH_2OH \longrightarrow$$

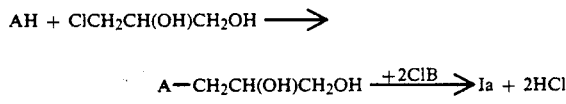

$$A-CH_2CH(OH)CH_2OH \xrightarrow{+2ClB} Ia + 2HCl$$

9) If $R_5$ is a group

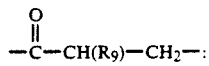

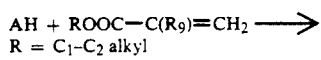

$R = C_1-C_2$ alkyl

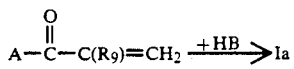

or alternatively:

$$HB + CH_2=C(R_9)-COOR \longrightarrow$$

$$ROOC-CH(R_9)CH_2-B \xrightarrow{+AH} Ia + ROH$$

10) If $R_5$ is a group $-CH_2-CH(OH)-CH_2-Y-(CH_2)_n-$:

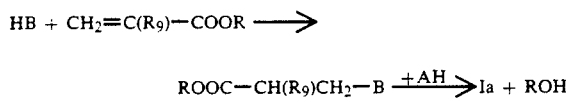

The reactions can be carried out in a manner known per se, with or without a solvent. It is preferred to carry out those reactions in which HCl evolves in the presence of an equivalent amount of a base, conveniently a tertiary amine. Transesterifications are preferably carried out in the presence of basic (nucleophilic) catalysts and distilling off the resulting ROH from the reaction mixture. Additions of olefinic groups to hydrogen silanes can be carried out in the presence of catalytic amounts of chloroplatinic acid.

If $R_{10}$ is a group of formula III, then the above reactions are carried out with a dichlorosilane or dihydrogen silane or with a α,ω-dihydrogen- or dichloropolysiloxane and by adding 2 equivalents of the triazine derivative.

If $R_{11}$ is a group of formula III and p is greater than 1, then such compounds can be prepared by hydrolysis and condensation of suitable dialkoxy- or dichlorosilanes of formula III

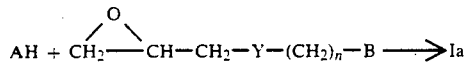

wherein Z=Cl or $C_1-C_4$alkoxy.

Compounds of formula Ib, wherein r is greater than 1, may be conveniently prepared by hydrolysis and condensation of suitable dialkoxy- or dichlorosilanes of formula

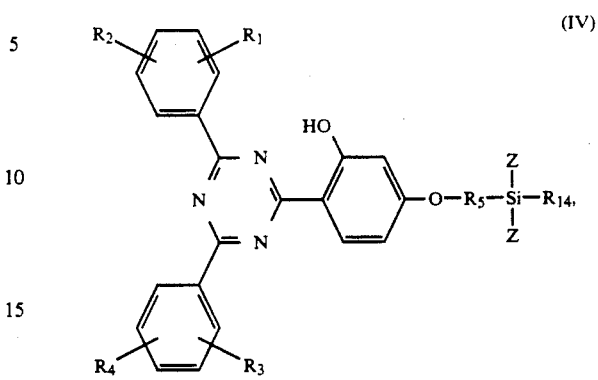

wherein Z is $C_1-C_4$alkoxy or a chlorine atom. The reaction can likewise be carried out in per se known manner, conveniently by addition of a base, as of an alkali metal hydroxide, to a solution of the compound of formula IV and heating the mixture.

The compounds of formula Ib, wherein r=1, as well as the compounds of formula IV, can be prepared by the methods described above in connection with the preparation of the compounds of formula Ia.

Compounds of formula Ia, wherein p is 0 and $R_{10}$, $R_{11}$ and $R_{12}$ are alkoxy, can also be used in the above reaction. In this case, the compounds of formula Ia are initially hydrolysed, their Si-alkoxy bonds being cleaved to form hydroxyl groups. Two molecules of the intermediate formed containing free Si—OH functions rapidly enter into a condensation reaction. Initially dimeric products, and in the later reaction course oligomeric products, are formed, such that one silicon atom of the starting monomer can be linked directly through an oxygen bridge to one, two or three units of the starting compound. The oligomeric products contain, after completion of the reaction, 2 to 50, preferably 3 to 10, units of the starting compound. The slower reaction step which determines the reaction rate is the hydrolysis in which the corresponding alkyl alcohol is split off.

The reaction can be carried out in per se known manner. Conveniently at least 0.3 equivalent, based on the starting compound, of a hydrolysing reagent is added to the starting compound of formula Ia. A minor amount of water must be present. Suitable hydrolysing reagents are acids or bases, typically sulfuric acid, phosphoric acid or a hydrohalic acid as acid, or an alkali metal hydroxide, typically calcium hydroxide, ammonia or an amine as base. Hydrochloric acid (HCl) is the preferred reagent. The starting compound as well as the hydrolysing reagent should be in liquid form, if appropriate as solution in a solvent. If the starting compound is added in a solvent, particularly suitable solvents are aromatic solvents or ethers, typically diglyme (bis[2-methoxyethyl]ether), tetrahydrofuran, dioxan, toluene, benzene or xylenes. The starting compound may be in the form of a 10% solution. The hydrolysing reagent is preferably used in concentrated aqueous solution. The reaction temperature is not critical and may be in the range from 0° to 150° C. The preferred reaction temperature is in the range from 50° to 150° C., and is typically 100° C. or, as the case may be, is at or close to the boiling point of the solvent. If a volatile hydrolysing reagent is used, working up can be effected by concentrating the reaction mixture by evaporation. Alternatively the product can be dissolved from the reaction mixture with a suitable organic solvent, such as hexane, or from the residue left after evaporation, and obtained from this solution by concentration.

Three-dimensionally crosslinked oligomeric products so obtained have properties similar to those of the compounds of formula Ib. Accordingly, the invention also relates to a mixture of oligomeric compounds obtainable by hydrolysis and condensation of compounds of formula Ia, wherein p is 0 and $R_{10}$, $R_{11}$ and $R_{12}$ are $C_1$–$C_{18}$alkoxy.

The starting compounds for the reactions 1-9 are known compounds. Some are commercially available.

Further details respecting the preparation of the compounds of formula Ia or Ib will be found in the Examples.

The compounds of formula Ia and Ib may be used with advantage as stabilisers for protecting organic polymers from degradation caused by light, oxygen and heat. Hence the invention further relates to a method of stabilising organic polymers against degradation caused by light, oxygen and heat, which comprises incorporating in said materials at least one compound of formula Ia and/or Ib. Representatives of such polymers are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which may be crosslinked), for example high density polyethylene (HDPE), low density polyethylene (LDPE), linear low density polyethylene (LLDPE), branched low density polyethylene (BLDPE).

2. Mixtures of the polymers mentioned in 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/but-1-ene, propylene/butadiene, isobutylene/isoprene, ethylene-/alkyl acrylates, ethylene/alkyl methacrylates, ethylene/vinyl acetate copolymers and their copolymers with carbon monoxide or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1) above, for example polypropylene/ethylene-propylene-copolymers, LDPE-/ethylene-vinyl acetate copolymers (EVA), LDPE-/ethylene-acrylic acid copolymers (EAA), LLDPE/EVA, LLDPE/EAA and random or alternating polyalkylene/carbon monoxide-copolymers as well as mixtures thereof with other polymers, for example polyamides.

3a. Hydrocarbon resins (for example $C_5$–$C_9$) and hydrogenated modifications thereof (for example tackifiers) and mixtures of polyalkylenes and starch.

4. Polystyrene, poly(p-methylstyrene), poly($\alpha$-methylstyrene).

5. Copolymers of styrene or $\alpha$-methylstyrene with dienes or acrylic derivatives, such as, for example, styrene/butadiene, styrene/acrylonitrile, styrene/alkyl methacrylate, styrene/maleic anhydride, styrene/butadiene/alkyl acrylate, styrene/butadiene/alkyl methacrylate styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or $\alpha$-methylstyrene, for example styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed in 5), for example the copolymer mixtures known as ABS, MBS, ASA or AES polymers.

7. Halogen-containing polymers, such as polychloroprene, chlorinated rubbers, chlorinated or sulfochlorinated polyethylene, copolymers of ethylene and chlorinated ethylene, epichlorohydrin homo- and copolymers, polymers of halogenated vinyl compounds, for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from $\alpha,\beta$-unsaturated acids and derivatives thereof, such as polyacrylates and polymethacrylates, polymethyl methacrylate impact-modified with butyl acrylate, polyacrylamides and polyacrylonitriles.

9. Copolymers of the monomers mentioned in 8) with each other or with other unsaturated monomers, for example acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene and those polyoxymethylenes which contain ethylene oxide as comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes derived from polyethers, polyesters or polybutadienes with terminal hydroxyl groups on the one hand and aliphatic or aromatic polyisocyanates on the other, as well as precursors thereof (polyisocyanates, polyols or prepolymers).

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides obtained by condensation of m-xylene, diamine and adipic acid; polyamides prepared from hexamethylenediamine and isophthalic acid and/or terephthalic acid and optionally an elastomer as modifier, for example poly(2,4,4,-trimethylhexamethylene) terephthalamide or poly-m-phenylene isophthalamide. Further copolymers of the aforementioned polyamides with polyolefins, olefin copolymers, ionomers or chemically bonded or grafted elastomers; or with polyethers, as with polyethylene glycols, polypropylene glycols or polytetramethylene glycols. Polyamides or copolyamides modified with EPDM or ABS. Polyamides condensed during processing (RIM polyamide systems).

16. Polyureas, polyimides and polyamide-imides.

17. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly[2,2-(4-hydroxyphenyl)-propane] terephthalate and polyhydroxybenzoates as well as block-copolyether-esters derived from polyethers having hydroxyl end groups.

18. Polycarbonates and polyester carbonates.

19. Polysulfones, polyether sulfones and polyether ketones.

20. Crosslinked polymers which are derived from aldehydes on the one hand and phenols, ureas and melamines on the other, such as phenol/formaldehyde resins, urea/formaldehyde resins and melamine/formaldehyde resins.

21. Drying and non-drying alkyd resins.

22. Unsaturated polyester resins derived from copolyesters of saturated and unsaturated dicarboxylic acids with polyhydric alcohols and vinyl compounds as crosslinking agents, and also halogenated modifications thereof of low inflammability.

23. Thermosetting acrylic resins derived from substituted acrylic esters, such as epoxy acrylates, urethane acrylates or polyester acrylates.

24. Alkyd resins, polyester resins or acrylate resins in admixture with melamine resins, urea resins, polyisocyanates or epoxy resins as crosslinking agents.

25. Crosslinked epoxy resins which are derived from polyepoxides, for example from bisglycidyl ethers or from cycloaliphatic diepoxides.

26. Natural polymers, such as cellulose, rubber, gelatin and chemically modified homologous derivatives thereof, such as cellulose acetates, cellulose propionates and cellulose butyrates, or the cellulose ethers, such as methyl cellulose; rosins and their derivatives.

27. Mixtures of polymers as mentioned above, for example PP/EPDM, polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

The use of the novel compounds as stabilisers in surface-coating compositions of all kinds is especially preferred. The invention thus relates to a method as described above, wherein the organic polymer is a binder for a surface-coating composition. Surface-coating compositions, i.e. paint or varnish compositions, which contain the compounds of formula Ia and/or Ib may be, for example, pigmented or unpigmented paint or varnish compositions or metallic paints. They may contain an organic solvent or be solventless, or they may be water-based paints.

The surface-coating compositions may contain as binder a polymer selected from those cited previously. Illustrative examples of surface-coating compositions containing special binders are the following:

1. surface-coating compositions based on cold- or hot-crosslinkable alkyd, acrylate, polyester, epoxy or melamine resins or mixtures of said resins, to which an optional acid curing catalyst is added;
2. two-component polyurethane surface-coating compositions based on hydroxylated acrylate, polyester or polyether resins and aliphatic or aromatic polyisocyanates;
3. single component polyurethane surface-coating compositions based on blocked polyisocyanates which are deblocked during stoving;
4. two-component surface-coating compositions based on (poly)ketimines and aliphatic or aromatic polyisocyanates;
5. two-component surface-coating compositions based on (poly)ketimines and an unsaturated acrylate resin or a polyacetoacetate resin or a methyl acrylamidoglycolate methyl ester;
6. two-component surface-coating compositions based on carboxyl or amino group containing polyacrylates and polyepoxides;
7. two-component surface-coating compositions based on anhydride group containing acrylate resins ad a polyhydroxy or polyamino component;
8. two-component surface-coating compositions based on (poly)oxazolidines and anhydride group containing acrylate resins or unsaturated acrylate resins or aliphatic or aromatic polyisocyanates;
9. two-component surface-coating compositions based on unsaturated polyacrylates and polymalonates;
10. thermoplastic polyacrylate surface-coating compositions based on thermoplastic acrylate resins or not self-crosslinking acrylate resins in conjunction with etherified melamine resins;
11. surface-coating systems based on siloxane-modified or fluorine-modified acrylate resins.

The surface-coating compositions may also be photocurable compositions, in which case the binder consists of monomer or oligomer compounds which contain ethylenic double bonds and which are converted by actinic light or with electron beams into a crosslinked high molecular weight form. The binder is usually a mixture of such compounds.

The surface-coating compositions may be applied as single layer or two-layer systems, in which case the stabilisers of this invention are preferably added to the unpigmented topmost layer.

The surface-coating compositions can be applied to the substrates (metal, plastic, wood and the like) by the conventional techniques, for example by brushing, spraying, coating, immersion or electrophoresis.

The amount of stabiliser of formula Ia and/or Ib added will depend on the respective substrate and the intended end use. Normally amounts from 0.01 to 5% by weight will suffice. It is preferred to use from 0.05 to 3% by weight, based on the polymer to be stabilised. In the practice of this invention, polymers containing 0.01 to 5% by weight, more particularly 0.05 to 3% by weight, of at least one compound of formula Ia and/or Ib are preferred.

In certain cases it may be useful to use two or more compounds of formula Ia and/or Ib. Furthermore, one or more other stabilisers and/or other additives may be used concurrently, as typically the following types of compounds:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol, 2,6-di-nonyl-4-methylphenol, 2,4-dimethyl-6-(1'-methyl-undec-1'-yl)phenol, 2,4-dimethyl-6-(1'-methyl-heptadec-1'-yl)phenol, 2,4-dimethyl-6-(1'-methyl-tridec-1'-yl)phenol and mixtures thereof.

1.2. Alkylthiomethylphenols, for example 2,4-dioctylthiomethyl-6-tert-butylphenol, 2,4-di-octylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-Di-tert-butyl-4-methoxyphenol, 2,5-di-tert-butyl-hydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenylstearate, bis(3,5-di-tert-butyl-4-hydroxyphenyl)adipate.

1.4. Hydroxylated thiodiphenylethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl) dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.6. O-, N- and S-benzyl compounds, for example 3,5,3',5'-tetra(tert-butyl-4,4'-dihydroxydibenzyl) ether, octadecyl-4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.7. Hydroxybenzylated malonates, for example dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis-(3,5-di-tert-butyl-4-hydroxybenzyl)malonate.

1.8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Further Triazines, for example 2,4-bis[(octylmercapto-6-(3,5-di-tert-butyl-4-hydroxyanilino)]-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.10. Benzylphosphonates; for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of monoethyl 3,5-di-tert-butyl-4-hydroxybenzylphosphonate.

1.11. Acylaminophenols, for example 4-hydroxylauryl anilide, 4-hydroxystearyl anilide, octyl N-(3,5-di-tertbutyl-4-hydroxyphenyl)carbamate.

1.12. Esters of β-(3,5-di-tertbutyl-4-hydroxyphenyl)propionic acid with monohydric or polyhydric alcohols, as with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo-[2.2.2]octane.

1.13. Esters of β-(5-tert-butyl-4-hydroxy-3-methylphenyl)propionic acid with monohydric or polyhydric alcohols, as with methanol, ethanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo-[2.2.2]octane.

1.14. Esters of β-(3,5-dicyclohexyl-4-hydroxyphenyl)propionic acid with monohydric or polyhydric alcohols, as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of 3,5-di-tert-butyl-4-hydroxyphenylacetic acid with monohydric or polyhydric alcohols, as with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis(hydroxyethyl)oxalyl diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV Absorbers and light stabilisers 2.1. 2-(2'-Hydroxyphenyl)benzotriazoles, for example the 5'-methyl-, 3',5'-di-tert-butyl, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octyloxy-, 3',5'-di-tert-amyl- or 3',5'-bis(α,α-dimethylbenzyl)- mixture of 5-chloro-3'-tert-butyl-5'-(2-octyloxycarbonylethyl)-and 5-chloro-3'-tert-butyl-5'-[2-(2-ethylhexyloxy)-carbonylethyl]-, 5-chloro-3'-tert-butyl-5'-(2-methoxycarbonylethyl)-, 3'-tert-butyl-5'-(2-methoxycarbonylethyl)-, 3'-tert-butyl-5'-(2-octyloxycarbonylethyl)-, 3'-tert-butyl-5'-[2-(2-ethylhexyloxy)-carbonylethyl]-, 3'-dodecyl-5'-methyl- and 3'-tert-butyl-5'-(2-isooctyloxycarbonylethyl)-2'-hydroxyphenyl-2H-benzotriazol-2-yl, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$C-H$_2$—COO(CH$_2$)$_3$]$_2$, wherein R=3'-tert-butyl-4'-hydroxy-5'-2H-benzotriazol-2-ylphenyl.

2.2. 2-Hydroxybenzophenonee, for example the 4-hydroxy, 4-methoxy, 4-octoxy, 4-decyloxy, 4-dodecyloxy, 4-benzyloxy, 4,2',4'-trihydroxy, 2'-hydroxy-4,4'-dimethoxy derivative.

2.3. Esters of unsubstituted or substituted benzoic acids, for example 4-tertbutylphenyl salicylate, phenyl salicylate, octylphenyl salicylate, dibenzoyl resorcinol, bis(4-tert-butylbenzoyl) resorcinol, benzoyl resorcinol, the 2,4-di-tertbutylphenyl ester of 3,5-di-tert-butyl-4-hydroxybenzoic acid, hexadecyl 3,5-di-tert-butyl-4-hydroxybenzoate, octadecyl 3,5-di-tert-butyl-4-hydroxybenzoate, the 2-methyl-4,6-di-tert-butylphenyl ester of 3,5-di-tert-butyl-4-hydroxybenzoic acid.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1- or 1:2 complex, with or without additional ligands, as n-butylamine, triethanolamine or N-cyclohexyl-diethanolamine, nickel dibutyl dithiocarbamate, nickel salts of monoalkyl esters of 4-hydroxy-3,5-di-tert-butylbenzylphosphonic acid, as of methyl or ethyl esters, nickel complexes of ketoximes, as of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, the bis(1,2,2,6,6-pentamethylpiperidyl) ester of n-butyl-3,5-di-tert-butyl-4-hydroxybenzylmalonic acid, the condensate of 1-hydroxyethyl-2,2,6,6-tetramethyl-4-hydroxypiperidine and succinic acid, the condensate of N,N'-bis(2,2,6,6-tetramethyl-4-piperidyl)-hexamethylenediamine and 4-tertoctylamino-2,6-dichloro-1,3,5-s-triazine, tris(2,2,6,6-tetramethyl-4-piperidyl)-nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decane-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)-pyrrolidine-2,5-dione.

2.7. Oxamides, for example 4,4'-dioctyloxyoxanilide, 2,2'-dioctyloxy-5,5'-di-tertbutoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxy-phenyl)-4,6-bis(2,4-dimethylphenyl)-1,3,5-triazine, 2-(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butoxy-propoxy)phenyl]-4,6-bis(2,4-dimethylphenyl)-1,3,5-triazine, 2-[2-hydroxy-4-(2-hydroxy-3-octyloxy-propoxy)-phenyl]-4,6-bis(2,4-dimethylphenyl)-1,3,5-triazine.

3. Metal deactivators, for example N,N'-diphenyloxamide, N-salicylal-N'-salicyloylhydrazine, N,N'-bis(salicyloyl)hydrazine, N,N'-bis(3,5-di-tertbutyl-4-hydroxyphenylpropionyl)hydrazine, 3-salicyloylamino-1,2,4-triazole, bis(benzylidene)oxalic dihydrazide, oxanilide, isophthalic dihydrazide, sebacic bis(phenylhydrazide), N,N'-diacetaladipic dihydrazide, N,N'-bis(salicyloyl)oxalic dihydrazide, N,N'-bis(salicyloyl)thiopropionic dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, bis(2,6-di-tert-butyl-4-methylphenyl)pentaerythritol diphosphite, bis(isodecyloxy)pentaerythritol diphosphite, bis(2,4-di-tert-butyl-6-methylphenyl)-pentaerythritol diphosphite, bis(2,4,6-tri-tert-butylphenyl)pentaerythritol diphosphite, tristearylsorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyldibenzo[d,g]-1,3,2-dioxaphosphocine.

5. Compounds which decompose peroxide, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in conjunction with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, fluorescent whitening agents, flameproofing agents, antistatic agents and blowing agents.

Particularly important stabilised polymers are those having an additional content of a light stabiliser selected from the class of the sterically hindered amines and/or the class of the 2-(2'-hydroxyphenyl)benzotriazoles. By sterically hindered amines are meant in particular those compounds which contain in the molecule one or more groups of formula

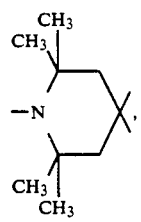

which compounds may be monomeric, oligomeric or polymeric. Examples of such compounds will be found in item 2.6 of the list of possible additional stabilisers.

The incorporation of the compounds of formula Ia or Ib and further optional additives in the polymers can be made before or during the processing of the polymers to shaped articles, conveniently by blending them in powder form or by addition to the melt or solution of the polymer or to a suitable surface-coating composition which contains a polymeric binder.

The invention therefore also relates to the polymers stabilised by addition of at least one compound of formula Ia or Ib, which polymers may contain other optional modifiers. The stabilised polymers can be used in different forms, as for example filaments, sheets, ribbons, profiles, hollow bodies, boards, double-walled boards, or as binders for paints and varnishes, adhesives and putty. Their use in surface-coating compositions is of particular interest.

The invention is illustrated in more detail by the following non-limitative Examples in which parts and percentages are by weight.

EXAMPLE 1

With stirring, a solution of 20 g of 2-(2,4-dihydroxyphenyl)-4,6-bis(2,4-dimethylphenyl)-1,3,5-triazine, 11,6 g of 3-triethylsilylpropyl glycidyl ether and 1.61 g of tetrabutylammonium bromide in 200 ml of xylene is heated for 16 h to 140° C. After cooling to room temperature, the reaction mixture is filtered and the filtrate is concentrated under vacuum. The oily residue is purified by chromatography on silica gel (eluant ethyl acetate/hexane 1:10), giving 16 g of the compound

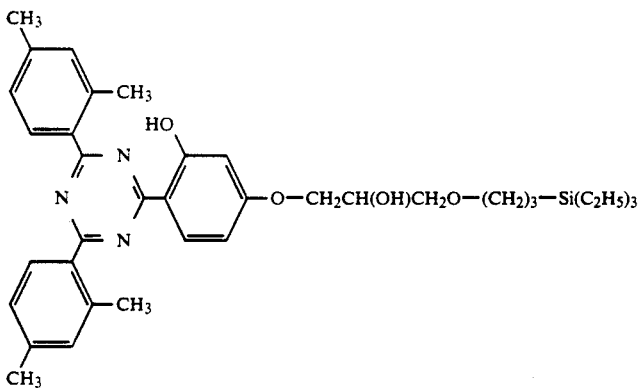

as a yellow oil.

| Analysis | calcd: | C 70.77 | H 7.86 | N 6.69 | Si 4.47% |
|---|---|---|---|---|---|
| (C₃₇H₄₉N₃O₄Si) | found: | C 70.13 | H 7.99 | N 6.11 | Si 4.34% |

EXAMPLE 2

A mixture of 16 g of 2-[2-hydroxy-4-(2-hydroxyethoxy)phenyl]-4,6-di(2,4-dimethylphenyl)-1,3,5-triazine, 7.64 g of tert-butyl dimethylchlorosilane and 6.86 g of imidazole in 100 ml of dimethyl formamide is stirred for 24 h at room temperature. The reaction mixture is diluted with 300 ml of ethyl acetate and filtered. The filtrate is concentrated by evaporation under vacuum and the residue is purified by chromatography (as in Example 1). The resultant crystalline product is recystallised from ethyl acetate/hexane, giving 9 g of the compound

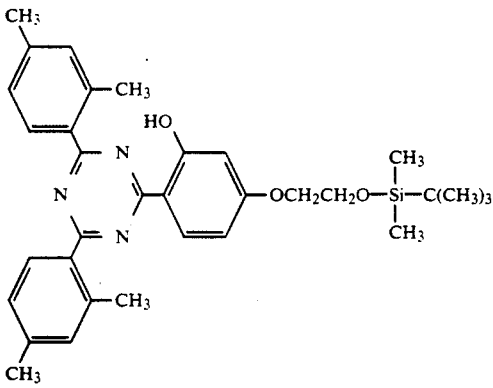

in the form of colourless crystals which melt at 131.5°-133.9° C.

| Analysis | calcd: | C 71.32 | H 7.44 | N 7.56 | Si 5.05% |
|---|---|---|---|---|---|
| (C₃₃H₄₁N₃O₃Si) | found: | C 71.38 | H 7.47 | N 7.41 | Si 4.76% |

EXAMPLE 3

A solution of 40 g of 2-(2,4-dihydroxyphenyl)-4,6-bis(2,4-dimethylphenyl)-1,3,5-triazine, 13.1 g of 1-butylglycidyl ether and 1.1 g tetramethylammonium chloride in 200 ml of xylene is stirred under nitrogen for 50 h at 130° C. After cooling to 20°-25° C., the reaction mixture is filtered on silica gel and the filtrate is concentrated under reduced pressure, giving 31.2 g of a yellow oil.

4.71 g of tert-butyldimethylchlorosilane are added dropwise to a solution of 15.0 g of the resultant oil and 4.22 g of imidazole in 100 ml of N,N-dimethylacetamide, whereupon the mixture warms slightly. The mixture is kept for 12 h at 20°-25° C. and subsequently concentrated on a rotovap. The crude product so obtained is chromatographed on silica gel with a 20:1 mixture of hexane/ethyl acetate. Recrystallisation from hexane gives 16.0 g of the compound of formula

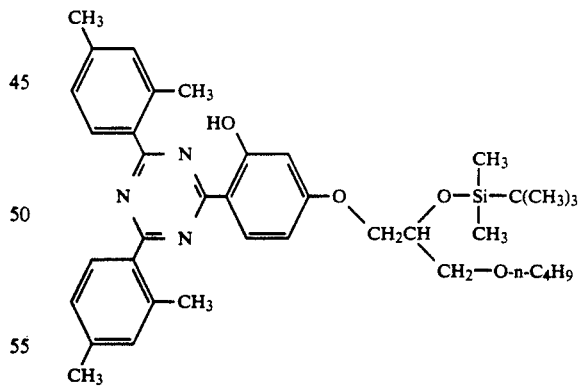

in the form of colourless crystals of m.p. 104°-107° C.

| Analysis | calcd: | C 71.10 | H 8.01 | N 6.55 | Si 4.38% |
|---|---|---|---|---|---|
| (C₃₈H₅₁N₃O₄Si) | found: | C 71.18 | H 7.98 | N 6.47 | Si 4.30% |

EXAMPLE 4

Example 3 is repeated, using 2-(2,4-dihydroxyphenyl)-4,6-diphenyl-1,3,5-triazine as starting material, to give the compound of formula

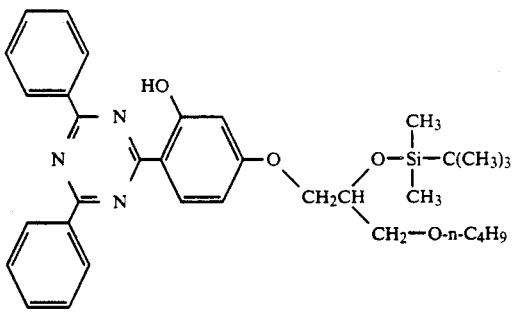

in the form of pale yellow crystals of m.p. 107°-108° C.

| Analysis | calcd: | C 69.71 | H 7.40 | N 7.17 |
|---|---|---|---|---|
| ($C_{34}H_{43}N_3O_4Si$) | found: | C 69.88 | H 7.64 | N 7.15 |

EXAMPLE 5

With stirring, a solution of 70 g 2-(2,4-dihydroxyphenyl)-4,6-bis(2,4-dimethylphenyl)-1,3,5-triazine, 25.9 g of ethyl chloroacetate and 48.7 g of potassium carbonate in 1000 ml of acetone is heated to 50° C. When the reaction is complete, the reaction mixture is cooled and filtered. The filtrate is concentrated and the residue is recrystallised from acetone, giving 49.0 g of a yellow product.

A suspension of 10.0 g of the above product, 2.0 g of dibutyltin oxide and 2.37 g of hydroxymethyltrimethylsilane in 50 ml toluene is heated, with stirring, for 16 h to 100° C. After cooling the reaction mixture to 20°-25° C., the crude product is purified on silica gel. Recrystallisation from hexane gives 7.0 g of the compound of formula

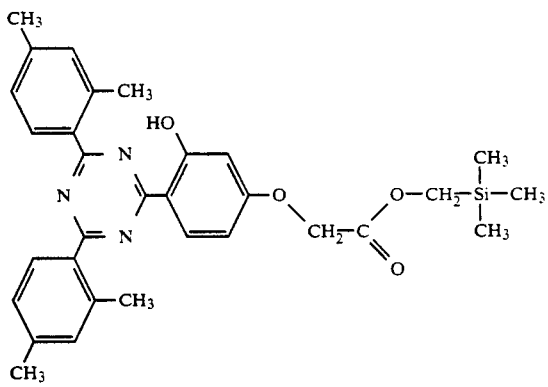

in the form of pale yellow crystals of m.p. 101°-103° C.

| Analysis | calcd: | C 68.73 | H 6.51 | N 7.76 | Si 5.18% |
|---|---|---|---|---|---|
| ($C_{31}H_{35}N_3O_4Si$) | found: | C 68.76 | H 6.49 | N 7.65 | Si 4.98% |

EXAMPLE 6

With stirring, a suspension of 11.0 g of 2-(2,4-dihydroxyphenyl)-4,6-bis(2,4-dimethylphenyl)-1,3,5-triazine, 5.0 g of 3-chloropropyltrimethylsilane and 7.1 g of potassium carbonate in 100 ml of N,N-dimethylacetamide is heated for 24 h to 100° C. The cooled mixture is filtered, the filtrate is concentrated and the residue is taken up in ethyl acetate. The solution is washed with water and then with a saturated solution of sodium chloride and dried over MgSO₄. The residue obtained after filtration and concentration of the filtrate is recrystallized from hexane, giving 10.2 g of the compound of formula

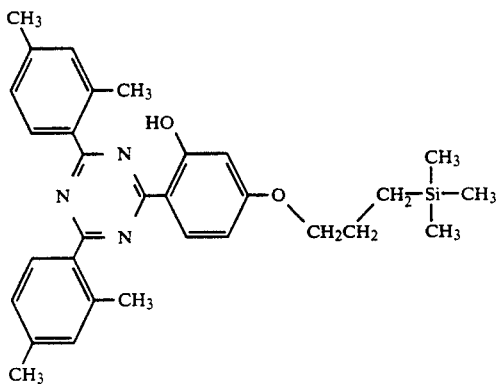

in the form of colourless crystals of m.p. 147°-149° C.

| Analysis | calcd: | C 72.76 | H 7.29 | N 8.21 |
|---|---|---|---|---|
| ($C_{31}H_{37}N_3O_2Si$) | found: | C 72.71 | H 7.29 | N 8.18 |

EXAMPLE 7

Example 6 is repeated, using 2-(2,4-dihydroxyphenyl)-4,6-diphenyl-1,3,5-triazine as starting material, to give the compound of formula

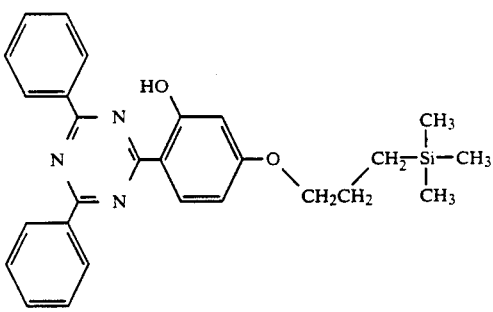

in the form of pale yellow crystals of m.p. 142°-143° C.

| Analysis | calcd: | C 71.17 | H 6.42 | N 9.22 |
|---|---|---|---|---|
| ($C_{27}H_{29}N_3O_2Si$) | found: | C 71.39 | H 6.42 | N 9.22 |

EXAMPLE 8

With stirring, a solution of 20 g 2-(2,4-dihydroxyphenyl)-4,6-bis(2,4-dimethylphenyl)-1,3,5-triazine, 6.6 g of 3-chloro-1,2-propanediol and 12.5 g of potassium carbonate in 150 ml of N,N-dimethylacetamide is heated for 24 h to 100° C. The cooled reaction mixture is filtered, the filtrate is concentrated and the residue is taken up in dichloromethane. The solution is washed with water and then with a saturated solution of sodium chloride, dried over MgSO₄ and filtered. The filtrate is concentrated by evaporation, giving 8.0 g of a pale yellow product.

The above product is stirred with 5.6 g of tert-butyldimethylchlorosilane and 5.06 g of imidazole in 50 ml of N,N-dimethylacetamide for 20 h at a temperature of 20°-25° C. The reaction solution is then concentrated by evaporation. The residue is taken up in ethyl acetate and the solution is filtered. The filtrate is concentrated and the residue is recrystallised from isopropanol, giving 7.9 g of the compound of formula

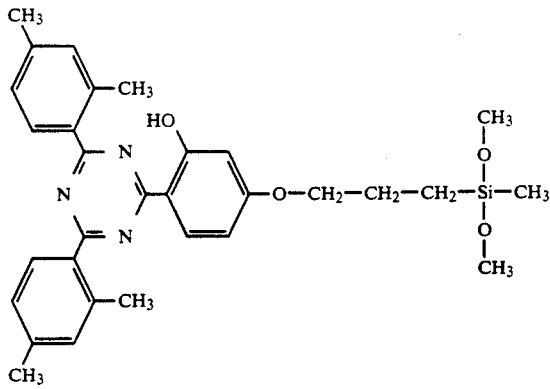

as a pale yellow oil.

EXAMPLE 9b

A solution of 10 g of the product of Example 9a and 0.96 g of an aqueous 33% solution of NaOH in 20 ml of diglyme is stirred for 24 h at 120° C. The reaction solution is purified by chromatography (silica gel; ethyl acetate), giving 9.0 g of a mixture of oligomers as a pale yellow resin, $M_n = 2000$ g/mol, $M_w = 2300$ g/mol, with a main component of formula

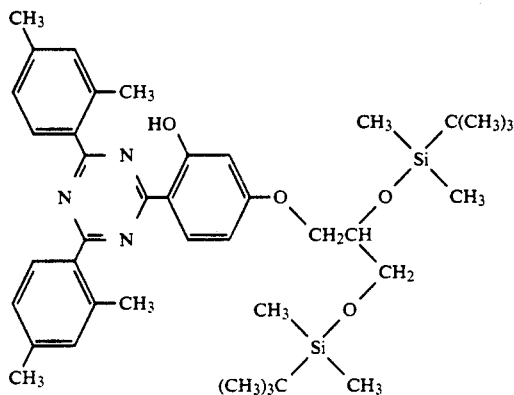

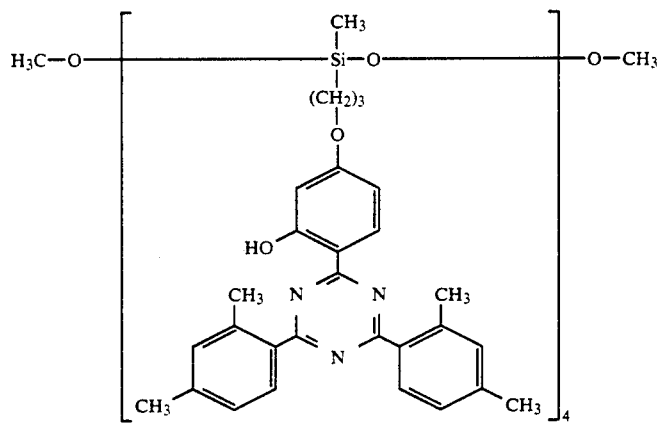

in the form of pale yellow crystals of m.p. 83°-88° C.

| Analysis | calcd: | C 68.62 | H 8.20 | N 6.00 |
|---|---|---|---|---|
| (C$_{40}$H$_{57}$N$_3$O$_4$Si$_2$) | found: | C 67.98 | H 8.25 | N 6.02 |

EXAMPLE 9a

With stirring, 27.6 g of 3-chloropropylmethyldimethoxysilane are added dropwise to a suspension of 50 g of 2-(2,4-dihydroxyphenyl)-4,6-bis(2,4-dimethylphenyl)-1,3,5-triazine and 32 g of potassium carbonate in 100 ml of N,N-dimethylacetamide. The mixture is heated, with stirring, for 15 h to 100° C. The cooled mixture is concentrated and the residue is purified by chromatography (silica gel: hexane/ethyl acetate 10:1), giving the compound of formula

EXAMPLE 10

With stirring, 9.3 g of (1-chloroethyl)trimethylsilane are added to a suspension of 25 g of 2-(2,4-dihydroxyphenyl)-4,6-bis(2,4-dimethylphenyl)-1,3,5-triazine and 16 g of potassium carbonate in 100 ml N,N-dimethylacetamide. The mixture is heated, with stirring, for 24 h to 100° C. The cooled mixture is concentrated and the residue is purified by chromatography (silica gel; hexane/ethyl acetate 50:1). Recrystallisation from toluene gives 9.8 g of the compound of formula

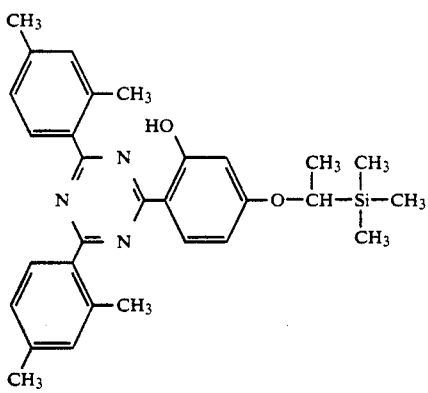

in the form of pale yellow crystals of m.p. 136°–138° C.

| Analysis | calcd: | C 72.40 | H 7.09 | N 8.44 |
|---|---|---|---|---|
| ($C_{30}H_{35}N_3O_2Si$) | found: | C 72.38 | H 7.09 | N 8.26 |

EXAMPLE 11

A suspension of 15 g of 2-(2,4-dihydroxyphenyl)-4,6-bis(2,4-dimethylphenyl-1,3,5-triazine, 5.55 g of chloromethyltrimethylsilane and 9.7 g of potassium carbonate in 100 ml of N,N-dimethylacetamide is heated, with stirring, for 24 h to 100° C. The cooled mixture is filtered and the filtrate is concentrated. The residue is taken up in dichloromethane and the solution is washed with water and then with a saturated solution of sodium chloride and dried over MgSO$_4$. The residue obtained after filtration and concentration of the filtrate is recrystallised from hexane, giving 6.7 g of the compound of formula

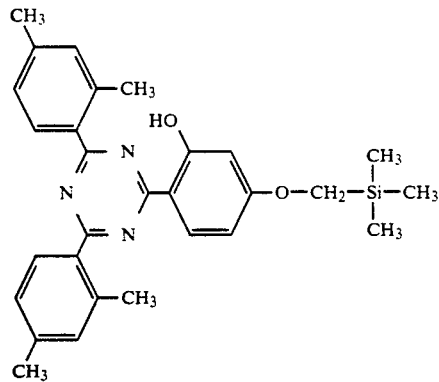

in the form of pale yellow crystals of m.p. 167°–170° C.

| Analysis | calcd: | C 72.01 | H 6.88 | N 8.69 |
|---|---|---|---|---|
| ($C_{29}H_{33}N_3O_2Si$) | found: | C 71.47 | H 6.91 | N 8.52 |

EXAMPLE 12

Example 11 is repeated, using 2-(2,4-dihydroxyphenyl)-4,6-diphenyl-1,3,5-triazine as starting material, to give the compound of formula

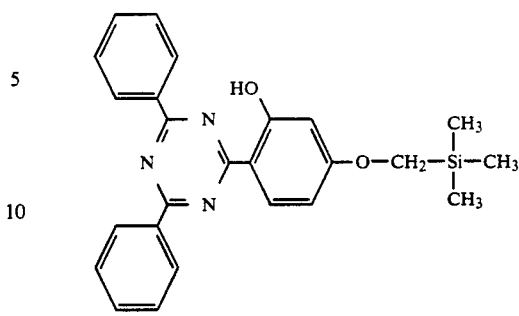

in the form of pale yellow crystals of m.p. 170°–172° C.

| Analysis | calcd: | C 70.23 | H 5.89 | N 9.83 |
|---|---|---|---|---|
| ($C_{25}H_{25}N_3O_2Si$) | found: | C 70.01 | H 5.92 | N 9.79 |

USE EXAMPLES

EXAMPLE 13

Aluminium sheets which have been primed with a white coil coat are coated with a silver metallic stoving lacquer based on polyester/cellulose acetobutyrate/melamine. A clear lacquer of the following composition is applied to this base coat:

54.5 parts of a 50% solution of an acrylic resin in xylene (Uracron ® XB 2263, DMS Resins BV)

16.3 parts of a 90% solution of a melamine resin (Cymel ® 327, Amer. Cyanamid Co.)

19.4 parts of xylene 5.5 parts of butyl glycol acetate 3.3 parts of butanol 1 part of a levelling agent (Baysilon ® A, Bayer AG)

This clear lacquer is blended with the stabilisers of Tables 1–3 in the form of a 10% solution in xylene. The amount added corresponds to 2% of stabiliser, based on the solids content of the clear lacquer.

After storage for 25 minutes at room temperature, the specimens are heated for 30 minutes to 130° C. The cured lacquer has a thickness of ca. 45 μm.

The specimens are subjected to weathering in an Atlas UVCON ® weathering apparatus with UVB-313 lamps at a cycle of 8 h UV irradiation at 70° C. and 4 h condensation at 50° C.

The 20° gloss of the specimens is measured according to DIN 67 530 at regular intervals. The initial value (20° gloss before the start of weathering) is set at 100%. Tables 1, 2 and 3 show the results of the gloss measurements after the indicated weathering time.

TABLE 1

| Stabilisers | 20° Gloss (in %) after | | | | |
|---|---|---|---|---|---|
| | 800 | 1600 | 2400 | 2800 | 3200 |
| | | | hours | | |
| none | 81 | 20 | | | |
| 2% of the product of Ex. 1 | 99 | 93 | 56 | 37 | 36 |
| 2% of the product of Ex. 2 | 98 | 94 | 76 | 20 | |
| 2% of the product of Ex. 2 +0.7% of HALS (I)* | 99 | 97 | 97 | 87 | 92 |

TABLE 2

| Stabilisers | 20° Gloss (in %) after | | | |
|---|---|---|---|---|
| | 1200 | 2400 | 3200 | 4000 |
| | hours | | | |
| none | 21 | | | |
| 2% of the product of Ex. 3 | 91 | 89 | | |
| 2% of the product of Ex. 3 +0.7% of HALS (I)* | 94 | 93 | 92 | 90 |

TABLE 3

| Stabilisers | 20° Gloss (in %) after | |
|---|---|---|
| | 800 | 1600 |
| | hours | |
| none | 78 | 28 |
| 2% of the product of Ex. 5 | 96 | 92 |
| 2% of the product of Ex. 6 | 80 | 79 |
| 2% of the product of Ex. 11 | 95 | 88 |

*HALS (I): bis(1,2,2,6,6-pentamethyl-4-piperidyl)sebacate.

What is claimed is:
1. A compound of formula Ia or Ib

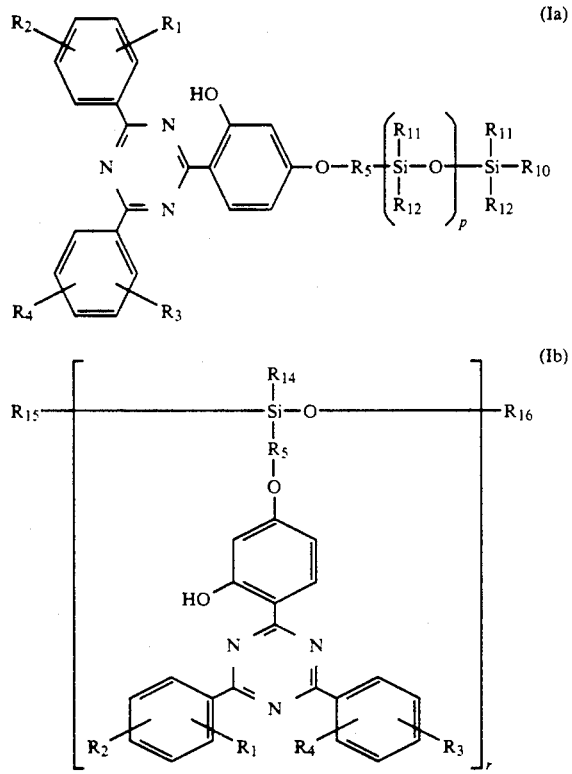

wherein p is 0 or an integer from 1-50, r is an integer from 1-50, $R_1$ and $R_3$ are each independently of the other hydrogen, OH, $C_1$-$C_{12}$alkyl or cyclohexyl, $R_2$ and $R_4$ are each independently of the other hydrogen, OH, $C_1$-$C_{12}$alkyl, $C_1$-$C_{18}$alkoxy, halogen or a group —O—II,

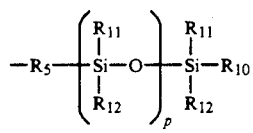

$R_5$ is a direct bond or a divalent group of one of the following formulae: —$C_mH_{2m}$—, —$(CH_2)_m$—O—, —$(CH_2)_m$—O—$R_6$—, —$(CH_2)_m$—CO—X—$(CH_2)_n$—, —$(CH_2)_m$—CO—X—$(CH_2)_n$—O—,

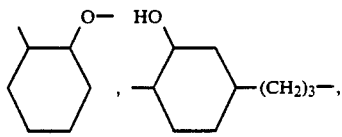

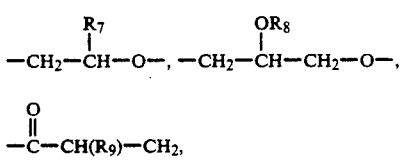

—$CH_2$—$CH(OH)$—$CH_2$—Y—$(CH_2)_m$—, wherein m and n are each independently of the other 1–4, $R_6$ is $C_1$-$C_{12}$alkylene, cyclohexylene or phenylene, $R_7$ is $C_1$-$C_{12}$alkyl, $C_5$-$C_8$cycloalkyl, phenyl, $C_2$-$C_{13}$alkoxymethyl, $C_6$-$C_9$cycloalkoxymethyl or phenoxymethyl, $R_8$ is a group of formula II, $R_9$ is hydrogen or methyl, X is —O— or —$NR_{13}$—, wherein $R_{13}$ is hydrogen, $C_1$-$C_{12}$alkyl, phenyl or a group —$(CH_2)_3$—II or —$(CH_2)_3$—O—II, Y is —O— or —NH—, $R_{10}$, $R_{11}$ and $R_{12}$ are each independently of one another $C_1$-$C_{18}$alkyl, cyclohexyl, phenyl or $C_1$-$C_{18}$alkoxy, and, if $R_2$ and $R_4$ are not a group —O—II, $R_{10}$ and/or $R_{11}$ may also be a group of formula III

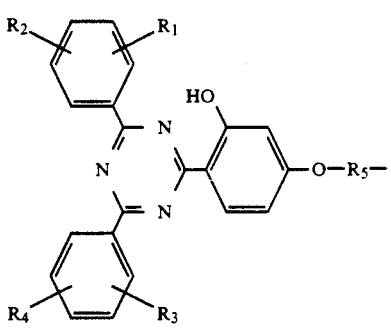

$R_{14}$ is $C_1$-$C_{12}$alkyl, $C_5$-$C_8$cycloalkyl or phenyl, and $R_{15}$ is hydroxy or $C_1$-$C_4$alkoxy and $R_{16}$ is hydrogen or $C_1$-$C_4$alkyl or, if r is greater than 2, $R_{15}$ and $R_{16}$ together may be a direct bond.

2. A compound according to claim 1 of formula Ia, wherein $R_5$ is a direct bond or a divalent group of one of the following formulae: —$(CH_2)_m$—, —$(CH_2)_m$—O—, —$(CH_2)_m$—O—$R_6$—, —$(CH_2)_m$—CO—X—$(CH_2)_n$—, —$(CH_2)_m$—CO—X—$(CH_2)_n$—O—,

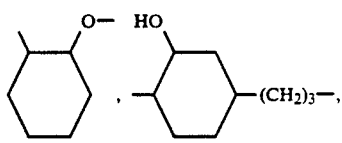

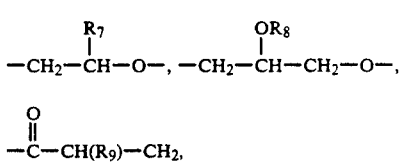

$-CH_2-CH(OH)-CH_2-Y-(CH_2)_m-$, wherein m and n are each independently of the other 1-4.

3. A compound according to claim 1 of formula Ia or Ib wherein $R_1$, $R_2$, $R_3$ and $R_4$ are each independently of one another hydrogen or methyl.

4. A compound according to claim 1 of formula Ia or Ib, wherein $R_{10}$, $R_{11}$ and $R_{12}$ are each independently of one another $C_1-C_8$alkyl, phenyl or $C_1-C_8$alkoxy, and $R_{14}$ is $C_1-C_8$alkyl or phenyl and, if $R_2$ and $R_4$ are not a group of formula II, $R_{10}$ and/or $R_{11}$ may also be a group of formula III.

5. A compound according to claim 4 of formula Ia or Ib, wherein $R_{10}$, $R_{11}$ and $R_{12}$ are each independently of one another $C_1-C_4$alkyl or $C_1-C_4$alkoxy and $R_{14}$ is $C_1-C_4$alkyl.

6. A compound according to claim 1 of formula Ia or Ib, wherein $R_5$ is a group $-C_mH_{2m}-$, $-(CH_2)_m-O-$, $-(CH_2)_m-CO-X-(CH_2)_n-$,

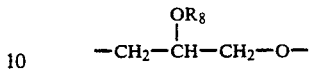

or $-CH_2-CH(OH)-CH_2-Y-(CH_2)_m-$, wherein m is 1, 2 or 3, $R_7$ is methyl, phenyl, $C_3-C_9$alkoxymethyl or phenoxymethyl, $R_8$ is a group of formula II and X and Y are each oxygen.

7. A compound according to claim 6 of formula Ia or Ib, wherein $R_5$ is a group $-C_mH_{2m}-$, $-(CH_2)_2-O-$, $-CH_2-CO-O-CH_2-$, $-CH_2-CH(O-C_4H_9)-O-$, $$-CH_2-\overset{\overset{OR_8}{|}}{CH}-CH_2-O-$$

or $-CH_2-CH(OH)-CH_2-O-(CH_2)_3-$, m is an integer 1, 2 or 3, and $R_8$ is tert-butyldimethylsilyl.

8. A compound according to claim 1 of formula Ia, wherein p is 0.

9. A compound according to claim 3 of formula Ia or Ib, wherein $R_1$, $R_2$, $R_3$ and $R_4$ are each in o- and/or p-position, p is 0, $R_5$ is $-(CH_2)_3-$, $R_{10}$ is methyl or ethyl, $R_{11}$ and $R_{12}$ are ethyl or ethoxy, $R_{14}$ is methyl, $R_{15}$ is $-OH$, methoxy or ethoxy, $R_{16}$ is hydrogen, methyl or ethyl, and, if r is greater than 2, $R_{15}$ and $R_{16}$ together may be a direct bond.

10. A mixture of oligomeric compounds obtainable by hydrolysis and condensation of a compound of formula Ia according to claim 1, wherein p is 0 and $R_{10}$, $R_{11}$ and $R_{12}$ are $C_1-C_{18}$alkoxy.

* * * * *